United States Patent
Kim et al.

(10) Patent No.: US 7,541,148 B2
(45) Date of Patent: Jun. 2, 2009

(54) METHOD FOR DETECTING BASE MUTATION

(75) Inventors: Nam-Keun Kim, Gyeonggi-do (KR); Suk-Joon Kim, Seoul (KR); Soo-Ok Kim, Seoul (KR); Eun-Ok Kim, Seoul (KR); Myung-Soon Moon, Seoul (KR); Wang-Don Yoo, Gyeonggi-do (KR); Chang-Hong Lee, Seoul (KR); Hyun-Jae Chung, Gyeonggi-do (KR); Mi-Sun Jee, Seoul (KR); Seong-Gyu Hwang, Seoul (KR); Sun-Pyo Hong, Seoul (KR)

(73) Assignee: Genematrix, Inc., Seoul (KR)

( * ) Notice: Subject to any disclaimer, the term of this patent is extended or adjusted under 35 U.S.C. 154(b) by 0 days.

(21) Appl. No.: 11/726,725

(22) Filed: Mar. 21, 2007

(65) Prior Publication Data

US 2007/0244313 A1 Oct. 18, 2007

Related U.S. Application Data

(63) Continuation of application No. 10/688,272, filed on Oct. 17, 2003, now Pat. No. 7,226,742.

(30) Foreign Application Priority Data

Oct. 18, 2002 (KR) ............... 10-2002-0063832
Sep. 2, 2003 (KR) ............... 10-2003-0061066

(51) Int. Cl.
*C12Q 1/68* (2006.01)
*C07H 21/02* (2006.01)
*C07H 21/04* (2006.01)

(52) U.S. Cl. ................. 435/6; 536/23.1; 536/24.3

(58) Field of Classification Search .......... 435/6; 536/23.1, 24.3

See application file for complete search history.

(56) References Cited

FOREIGN PATENT DOCUMENTS

WO   WO 01/90419 A2   11/2001

OTHER PUBLICATIONS

Shapero et al., SNP genotyping by multiplexed solid-phase amplification and fluorescent minisequencing. Genome Research 11 : 1926-1934 (2001).*
Hwang et al., "Detection Of Hepatitis B Virus Variants Associated With Lamivudine Resistance Using RFMP," *The Korean Journal of Hepatology*, 2003, vol. 9, Supp. 3 (w/ English translation).
Kim et al., "New Hepatitis C Virus Genotyping Assay As A Routine Method By Novel RFMP," *The Korean Journal of Hepatology*, 2003, vol. 9, Supp. 3 (w/ English translation).
Kim et al., "The Study Of Development Of Lamivudine Resistant Mutants And Viral Breakthrough," *The Korean Journal of Hepatology*, 2003, vol. 9, Supp. 3 (w/ English translation).
Kim et. al., "Novel Mass Spectrometric Assay for Monitoring Drug Resistance in Hepatitis B Virus during Lamivudine Therapy," *Korean J. Genetics*, 2003, 25(1):63-75.
New England Biolabs Catalog, 2000, pp. 192, 202 & 203.
Niesters, *J Med Microbiol.*, 2002, 51:695-699.
Nguyen, *J Med Virology*, 1998, 54:20-25.
Orita et al., Rapid and Sensitive Detection of Point Mutations and DNA Polymorphisms Using the Polymerase Chain Reaction. *Genomics*, 1989, 5:874-9.
Tobe et al., "Single-well genotyping of diallelic sequence variations by a two-color ELISA-based oligonucleotide ligation essay," *Nucleic Acids Research*, 1996, 24(19): 3728-32.
Pastinen et al., "Minisequencing: A Specific Tool for DNA Analysis and Diagnostics on Oligonucleotide Arrays," *Genome Research*, 1997, 606-14.

* cited by examiner

*Primary Examiner*—Ethan Whisenant
(74) *Attorney, Agent, or Firm*—Edwards Angell Palmer & Dodge LLP

(57) ABSTRACT

The present invention relates to methods for precisely and effectively detecting mutations of organism.

4 Claims, 9 Drawing Sheets

METHOD FOR DETECTING BASE MUTATION

This application is a continuation of the U.S. patent application Ser. No. 10/688,272, filed Oct. 17, 2003 now U.S. Pat. No. 7,226,742, which claims priority to Korean application 10-2003-0061066, filed Sep. 2, 2003, and to Korean application 10-2002-0063832, filed Oct. 18, 2002, the contents of each of which are incorporated herein by reference in their entireties.

1. FIELD OF THE INVENTION

The present invention relates to methods for determining genetic variation in an organism. Genetic analysis is used for disease risk, diagnosis, prognosis or disease treatment. For example, mutation analysis on a specific gene of a specific person makes it possible to predict the disease risk, thereby inducing prevention of the disease. Whether a virus that causes a disease has resistance to medicines is examined through mutation analysis, which results in effective treatment.

2. BACKGROUND OF THE INVENTION

Human genome project enables more broad measurement of disease risk, diagnosis or prognosis and prediction of reaction on medication. Nucleotide sequence analysis of a plurality of individuals presents polymorphic sites, which are referred to as SNPs (single nucleotide polymorphisms). The SNP is a variation occurred over the specific frequency in a nucleotide sequence of chromosome in organism. In human body, SNPs occur every about 1,000 bases. In consideration of the size of human genome, millions of SNPs exist in human body. Since the SNP is regarded as a means for explaining characteristic difference between individuals, the SNP can be used in prevention or treatment of disease by examination of cause of disease.

SNPs discovered by the human genome project show only that the polymorphism exist in human body but do not show how those polymorphisms are related to disease. In order to reveal the relationship between the SNPs and diseases, a comparative analysis of polymorphism pattern represented in healthy people and patients, SNP scoring, is required. For precise examination of the relationship between the SNP and disease, a large number of SNPs should be analyzed without error.

The SNP scoring method includes DNA sequencing, PCR-SSCP (Polymerase chain reaction—Single stranded conformation polymorphism), allele specific hybridization, oligo-ligation, mini-sequencing and enzyme cleavage method. A method using a DNA chip is also introduced, but it is not different from the allele specific hybridization in principle except its using a support adhering to oligonucleotide probe.

The two classical methods for carrying out DNA sequencing are the Maxam and Gilbert chemical procedure and the Sanger method that has been recently used. The DNA sequencing method is to find out nucleotide sequences of the whole or a part of genes rather than to examine genetic variations of specific sites. Since genetic variations of specific sites may be identified by examination of nucleotide sequences, the DNA sequencing method can be used in the SNP scoring. However, the DNA sequencing method is ineffective because adjacent nucleotide sequences that do not require examination are read with target SNP.

In PCR-SSCP (Orita, M. et al., Genomics, 1989, 5:8874-8879), sequences including SNPs to be analyzed are amplified by PCR, and then separated into each strand. Thereafter, electrophoresis is performed on polyacrylamide gel. Since the secondary structure of DNA strand is changed by difference of sequence, variations in sequence are examined from differences in electrophoresis running velocity resulting from the difference of structure.

The allele specific hybridization is to examine variations by hybridizing DNAs labeled with radioisotope to probes attached to a nylon filer, by regulating hybridization conditions such as temperature.

The oligo-ligation (Nucleic Acid Research 24, 3728, 1996) is to examine sequence variations by performing a reaction under a condition where it is not happened if target DNA is non-complementary with template DNAs and confirming whether the ligation is happened.

The mini-sequencing (Genome Research 7:606, 1997) is developed for SNP scoring. This method performs DNA polymerization in a condition that only one base of interest can be polymerized and distinguish what the polymerized base is.

The PCR-SSCP, the allele specific hybridization, the oligo-ligation are ineffective methods in analysis of many samples because of its use of polyacrylamide gel. And the errors resulting from mismatching of probes with undesired sites cannot be identified by those methods.

Although the mini-sequencing is simple and effective in analysis of many samples, the incorrect result by errors of mismatching cannot be still identified, and base deletion and insertion cannot be found by the mini-sequencing.

The enzyme cleavage method is also developed for SNP scoring (WO 01/90419). In the enzyme cleavage method, sequences to be analyzed are amplified by appropriate methods like the PCR. The amplified products include sequences that can be cleaved or recognized by two restriction enzymes. The enzyme cleavage method is to examine sequence variations by cleaving the amplified products with two restriction enzymes and measuring the molecular weight of the cleaved fragments. The enzyme cleavage has an advantage of simplicity and rapidity because the molecular weight of the fragments obtained from restriction enzyme reaction is measured by mass spectrometry right after amplification of genes by PCR. However, the incorrect analysis by errors is not identified by the enzyme cleavage method described in WO 01/90419. Although the incorrect analysis may be induced when primers are combined in undesired sites during the PCR, it is not identified. For example, the primer used to examine polymorphisms of CYP2C9 may be combined with CYP2C8. In this case, it is difficult to discover whether the errors are generated because whether the primer is combined with CYP2C8 other than CYP2C9 cannot be identified. This method can detect one base substitution, but cannot detect deletion or insertion. Also, substitution of adjacent two or more bases cannot be detected at the same time.

3. SUMMARY OF THE INVENTION

Accordingly, an object of the present invention is to provide a method for precisely and effectively detecting mutations of organism.

In order to achieve the above-described object, there is provided a method for precisely and effectively detecting mutations of organism in an embodiment of the present invention.

The present invention enables simple and rapid examination of mutations in many samples and precise examination of mutation by identification of errors resulting from binding of primers at incorrect regions. Moreover the present invention provides method of examining two or more sites of mutations, which are adjacent within 32 bases at the same time, and detecting deletion or insertion. Especially when there are various genotypes in an individual, it can be identified whether mutations in different sites simultaneously exist in one genotype or exist with mixed in different genotypes. For example, a human has a pair (two) of chromosomes having the same genetic information. When mutations occur it may occur either in the two chromosomes (homo) or in one chromosome (hetero). When two or more mutations of adjacent base are all hetero, those mutations may exist in one chromosome at the same time or in different chromosomes. Since the two cases may have different effect on life, those should be distinguished. In case of virus which infects human, various genotypes is mixed. When two or more mutations of adjacent bases are all hetero, it should be distinguished whether those mutations exist in one genotype at the same time or in different genotypes.

In order to analyze mutations, the method of present invention amplify desired sequence to include sites where the resulting product may be cleaved by restriction enzymes and the number of bases in the fragments cleaved by restriction enzymes is made to be less than 32 and at least one base among them is made to be produced by replication of template not primers itself and after the amplified fragments are cleaved by restriction enzymes, the molecular weight of the fragments is measured to analyze mutations.

In an embodiment, there is provided a method for detecting mutations, comprising: a) amplifying a target polynucleotide using a forward primer and a reverse primer; b) generating fragments of two or more single-stranded polynucleotides including one or more mutation sequences having the size of 2-32 bases by cleaving the amplified target polynucleotide with restriction enzymes; and c) measuring the molecular weight of the cleaved fragments.

Preferably, the amplified polynucleotide is cleaved to include one mutation among two or more different mutations in one single stranded polynucleotide fragment and all mutations in another single stranded nucleotide fragment. For example, when A and G in . . . ATG . . . are mutation sequences, a first single-stranded nucleotide fragment generated by restriction enzyme cleavage includes only A of the two mutation sequences, and a second single-stranded nucleotide includes both A and G.

In order to analyze mutations, the method of present invention amplify desired sequence to include sites where the resulting product may be cleaved by restriction enzymes and the cleaved fragments have a following structure.

more preferable. Preferably, the restriction enzymes are a restriction enzyme having a low optimum temperature selected from the group consisting of Fok1, Bbv I, Bsg I, Bcg I, Bpm I, BseR I and Bae I, and a restriction enzyme having a high optimum temperature selected from the group consisting of BstF5 I, Taq I, BsaB I, Btr I, BstAP I, Fau I, Bcl I, Pci I and Apo I. More preferably the restriction enzymes are Fok1 and BstF5 I.

The restriction enzymes having the relatively low optimum temperature are Bae I(25° C.), Fok1, Bbv I, Bsg I, Bcg I, Bpm I, BseR I, Mmel I and Ava II(37° C.). The enzymes having the relatively high optimum temperature are BstF5 I, Taq I (65° C.), BsaB I, Btr I, BstAP I (60° C.), Bcl I, Pci I and Apo I (50° C.).

One of the two primers used in PCR amplification comprises a primer binding sequence 1, a restriction enzyme recognition sequence and a primer binding sequence 2, and the other primer comprises a primer binding sequence 3.

The 'primer binding sequence' is a sequence that is complementary with nucleic acid to be template, but the restriction enzyme recognition sequence may not be complementary with nucleic acid. Since the number of bases of the primer binding sequences 1, 2 and 3 should be at least four or more bases to bind with template DNA. Since the primer was well combined with template DNA in the size of 8-30 bases, the number of bases preferably ranges from 8 to 30. The 'front sequence from mutation' is a sequence toward 5' of the mutation to be examined. The 'mutation sequence' is a sequence corresponding to a mutation to be examined. Substitution, insertion and deletion of bases may occur, wherein the number of bases is generally 1 and may be two or more. The 'sequence behind mutation' is a sequence toward 3' of the mutation sequence.

Preferably, the total number of bases of the front sequence from mutation and behind mutation is one or more. The fragments resulting from restriction enzyme cleavage should include mutation sequences, and the size of the fragment preferably ranges from 2 to 32 bases. More preferably, the size is 12 bases. The reason the size of cleaved fragments is limited is that there is a good result in case of the favorable size of fragments in mass spectrometry analysis. The above number of bases in fragments is preferable because the fragment having the size of over 32 bases is too large to examine mutations by measuring the molecular weight using mass spectrometry. And the fragment only having a base is not preferable because the fragment having only a mutation sequence disables identification of binding of primers at incorrect sites. Since the two restriction enzymes recognize

| 5'- | Primer binding sequence 1 | Restriction Enzyme recognition sequence | Primer binding sequence 2 | Front sequence from mutation | Mutation sequence | Sequence behind mutation | Primer binding sequence 3 | -3' |
|---|---|---|---|---|---|---|---|---|

The 'restriction enzyme recognition sequence' is a sequence simultaneously or adjacently recognized by different restriction enzymes, which may not correspond to a cleaved sequence. For example, both Fok1 and BstF5I recognize the sequence GGATG. But, the cleaved sites are next to the 9th/13th and 2nd/0th bases from the 3' end of the recognition sequence respectively. Both two restriction enzymes for recognizing the restriction enzyme recognition sequence may have the same optimum temperature or different optimum temperatures. The different optimum temperatures are the same or adjacent sites, it is preferable that the other restriction enzyme does not activate while one restriction enzyme reacts with the amplified product. When the amplified fragments are cleaved with restriction enzymes, reaction may be performed consecutively at different temperatures in consideration of the optimum temperatures of two restriction enzymes. Otherwise, the fragments may be cleaved with one restriction enzyme, and then with another restriction enzyme. Here, the cleavage by the first restriction enzyme should not remove or damage recognition sequences or its cleavage sites of the second restriction enzyme existing in the fragment including the mutation sequence.

4. BRIEF DESCRIPTION OF THE DRAWINGS

5. DETAILED DESCRIPTION OF THE PREFERRED EMBODIMENTS

EXAMPLE 1

Figure 1:
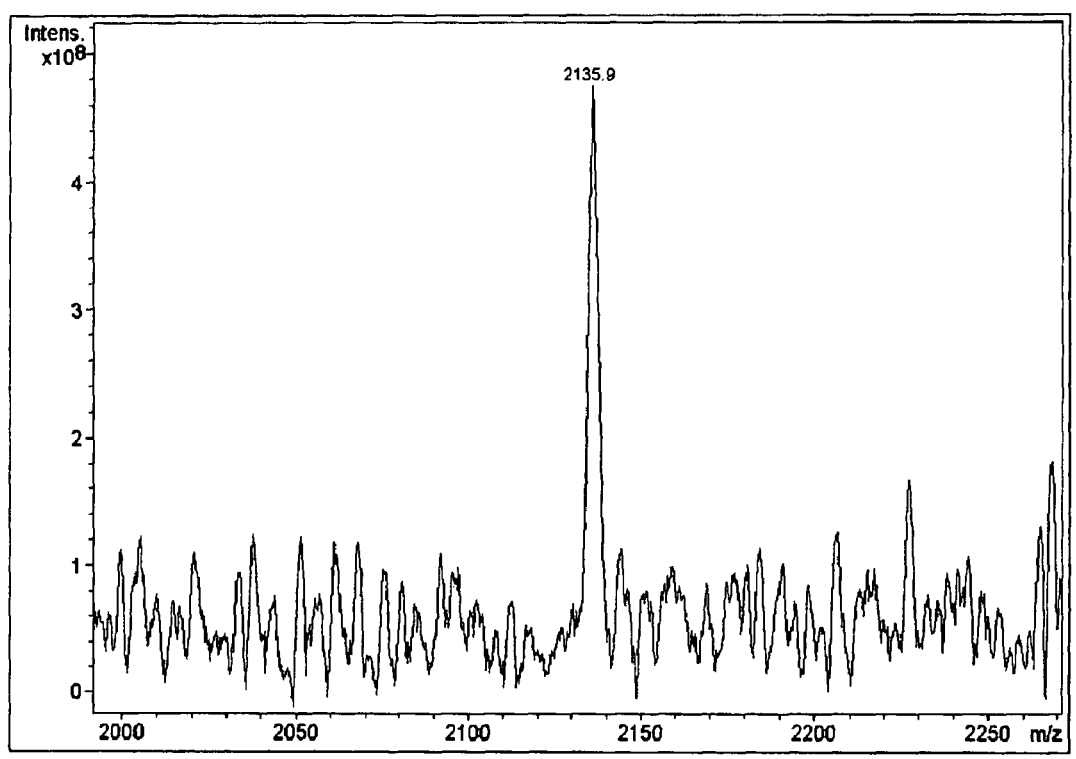
FIG. 1 shows the MALDI-TOF mass spectrum of the 7mer when the $2741^{st}$ base of the $4^{th}$ intron of human maspin (serpinb5) gene is normal (C/C).

Mutation of the $2741^{st}$ Base of the $4^{th}$ Intron of Human Maspin Gene

Mutation of the $2741^{st}$ base (rs1509477; the 61001755th base of chromosome No. 18) of the $4^{th}$ intron of human maspin (serpinb5) gene that is known as cancer metastasis inhibition gene is examined.

1. PCR Amplification and Restriction Enzyme Cleavage

The sequence (5'→3') of template DNA is as follows.

```
                                              (SEQ ID NO:1)
GTTTCACTTGATAAAGCAATAAAATGCTATTCAcAGCTGCATGAGGCTAC

AC CCTTCTTTTGAATGCAG
```

The bolded sequences are sites where the following primers 1 and 2 are hybridized. The bases represented by small letters are 'mutation sequence'.

```
Primer 1.
                                              (SEQ ID NO:2)
5'-TCACTTGATAAAGCAATAAAAggatgGCTATTCA-3' (34 mer)

Primer 2.
                                              (SEQ ID NO:3)
5'-CATTCAAAAGAAGGGTGTAGCCTCATGC-3' (28 mer)
```

The sequences represented by small letters are recognition sequences of Fok1 and BstF5I.

PCR buffer (1×), 2 mM of $MgSO_4$, 200 mM of dNTP, Platinum Taq Polymerase (Invitrogen, 10966-026) 0.315 U, 0.5 μM of primer 1 and 0.5 μM of primer 2, and 36 ng of genomic DNA were added to be 18 μl of the total reaction volume. Then, the PCR reaction was performed under the following condition.

94° C., 2 min.
94° C., 15 sec. 55° C., 15 sec. 72° C., 30 sec. (10 cycles),
94° C., 15 sec. 60° C., 15 sec. 72° C., 30 sec. (35 cycles)

The genomic DNA was isolated from blood and purified. For example, 'SDS/protease K' method (Maniatis, Molecular Cloning, A laboratory Manual, Cold Spring Harbor Laboratory Press, Cold Spring Harbor, 1989) or QIAamp DNA Mini Kit 250 (Qiagen 51106) could be used in isolation of DNA from blood. When the concentration of DNA is low, the DNA can be concentrated by the following method. First 1/10 volume of 3 M Sodium acetate (pH 5.3) and 2.5 volume of ethanol were added to DNA solution and gently mixed. The resulting solution was left at –20° C. for more than 1 hour, and then centrifuged at 4° C., 13000 rpm for 15 minutes. After the supernatant was removed, 70% ethanol was added and the resulting solution was centrifuged at 4° C., 13000 rpm for 10 minutes. Then, ethanol was dried, and desired volume of distilled water was added to the resulting solution.

The sequence of fragments obtained from the PCR is as follows (5'→3').

```
                                              (SEQ ID NO:4)
TCACTTGATAAAGCAATAAAAggatgGCTATTCA[C/T]AGCTGCATGAG

GCTACACCCTTCTTTTGAATG
```

```
                                              (SEQ ID NO:5)
AGTGAACTATTTCGTTATTTTcctacCGATAAGT[G/A]TCGACGTACTC

CGATGTGGGAAGAAAACTTAC
```

The sites represented by small letters are sequences recognized by Fok1 and BstF5I, the bolded sites are sequences of fragments generated by restriction enzyme cleavage, and the bases represented by brackets are 'mutation sequences'. To the reactant were added FokI (NEB R109L) 1 U, BstF5I (NEB, V0031L) 1 U, 50 mM of potassium acetate, 20 mM of Tris-acetate, 10 mM of magnesium acetate, 1 mM of DTT (pH 7.9 @ 25° C.). The resulting solution was reacted at 25° C. for 2 hours, and consecutively at 45° C. for 2 hours.

For optimization of enzyme reaction, the amplified products were reacted with FokI and BstF5I at 25° C., 37° C., 45° C., 55° C. and 65° C. As a result, 70% of enzyme reaction proceeded at 25° C., and more than 90% enzyme reaction proceeded at 37° C. in case of FokI. In case of BstF5I, the enzyme reaction didn't proceeded at 25° C. Accordingly, the products were preferably reacted first at 25° C. where only FokI could react, and then at over 37° C. where BstF5I could react.

2. Purification and Desalination

Preferably, DNA fragments were purely isolated from the above solution treated with restriction enzymes, and then the molecular weights of the fragments were measured. For example, Nucleave Genotyping Kit (Variagenics, USA) might be used. 70 μl of 1M TEAA (Triethylammoniumacetate, pH 7.6) was added to the restriction enzyme reaction solution, and left for 1 minute. 70 μl of 1M TEAA and 90 μl of the above mixed solution were added to a Sample Preparation Plate, and then 85 μl of 0.1M TEAA was five times passed through the Sample Preparation Plate. The Sample Preparation Plate was centrifuged at 1000 rpm for 5 minutes. Thereafter, the Sample Preparation Plate was placed on a Collection Plate, and then 60 µl of 60% isopropanol was added thereto and passed. When the effluent solution was collected in the Collection plate, the Collection Plate was dried at 115° C. for 75 minutes.

3. MALDI-TOF Mass Spectrometry

6 µl of MALDI matrix (22.8 mg ammonium citrate, 148.5 mg hydroxypicolinic acid, 1.12 ml acetonitrile, 7.8 ml H20) was added to the Collection Plate, and then 4 µl of mixture of the MALDI matrix and effluent solution was placed on an Anchor chip plate of MALDI-TOF (Biflex IV, Bruker). It was dried at 37° C. for 30 minutes, left at room temperature to be cooled for a while, and then subjected to MALDI-TOF analysis. The analysis method follows the MALDI-TOF manual.

Figure 2:
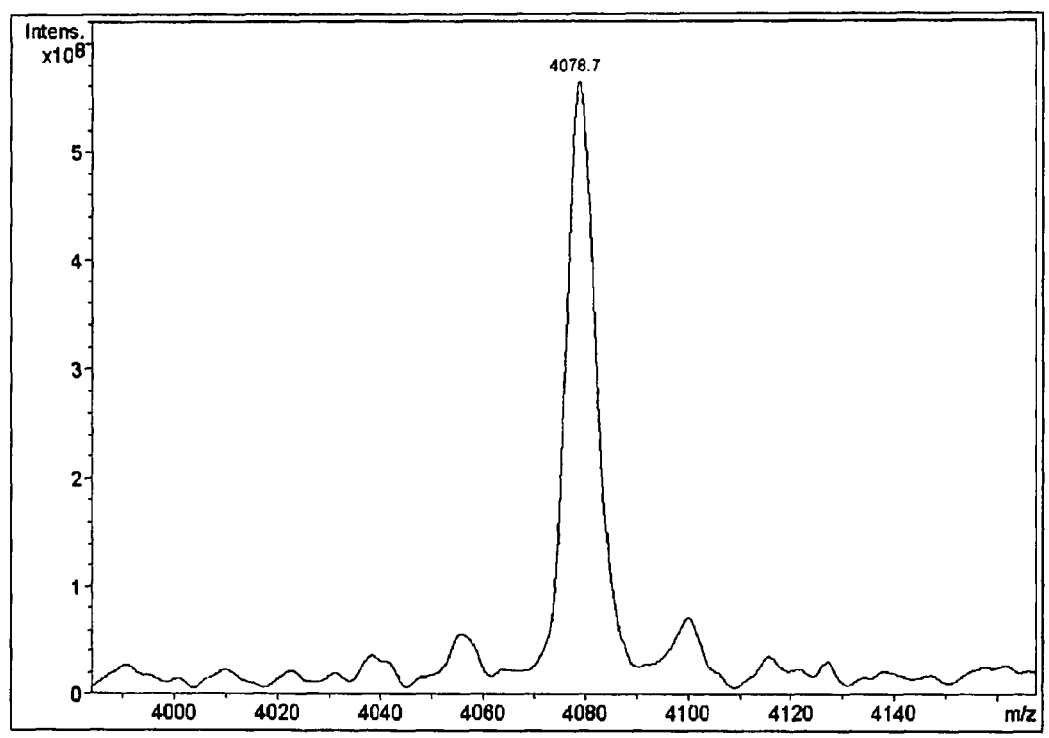
FIG. 2 shows the MALDI-TOF mass spectrum of the 13mer when the $2741^{st}$ base of the $4^{th}$ intron of human maspin gene is normal (C/C).
Figure 3:
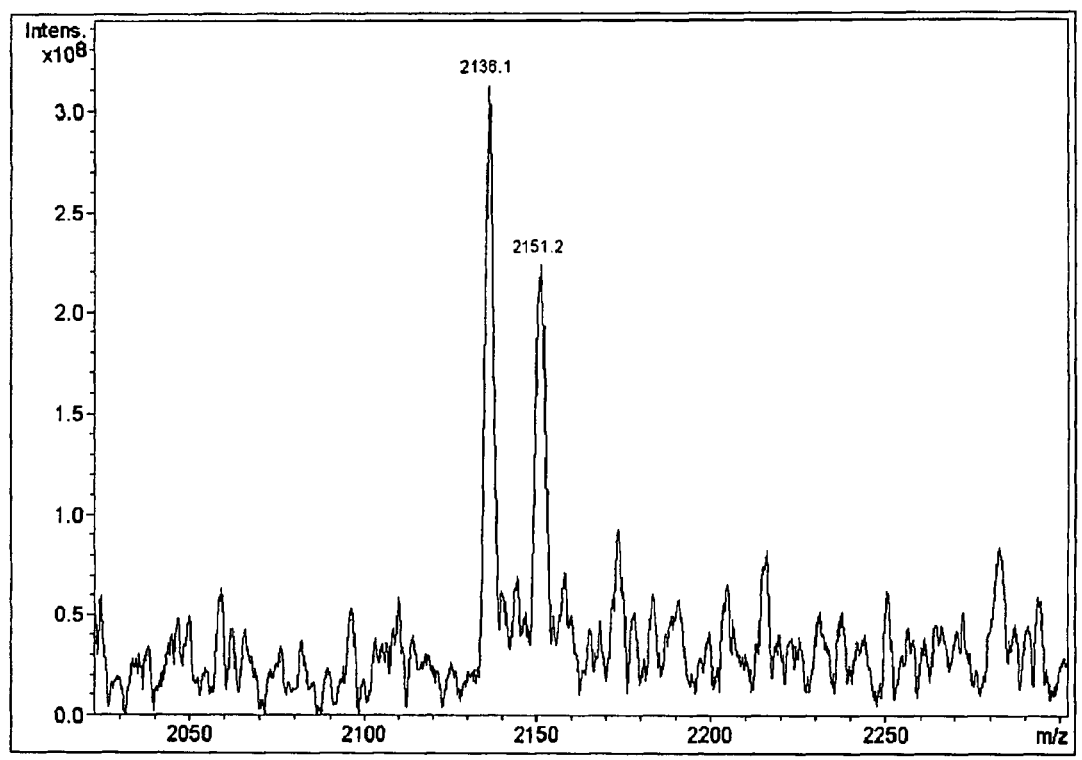
FIG. 3 shows the MALDI-TOF mass spectrum of the 7mer when the $2741^{st}$ base of the $4^{th}$ intron of human maspin gene is hetero (C/T).
Figure 4:
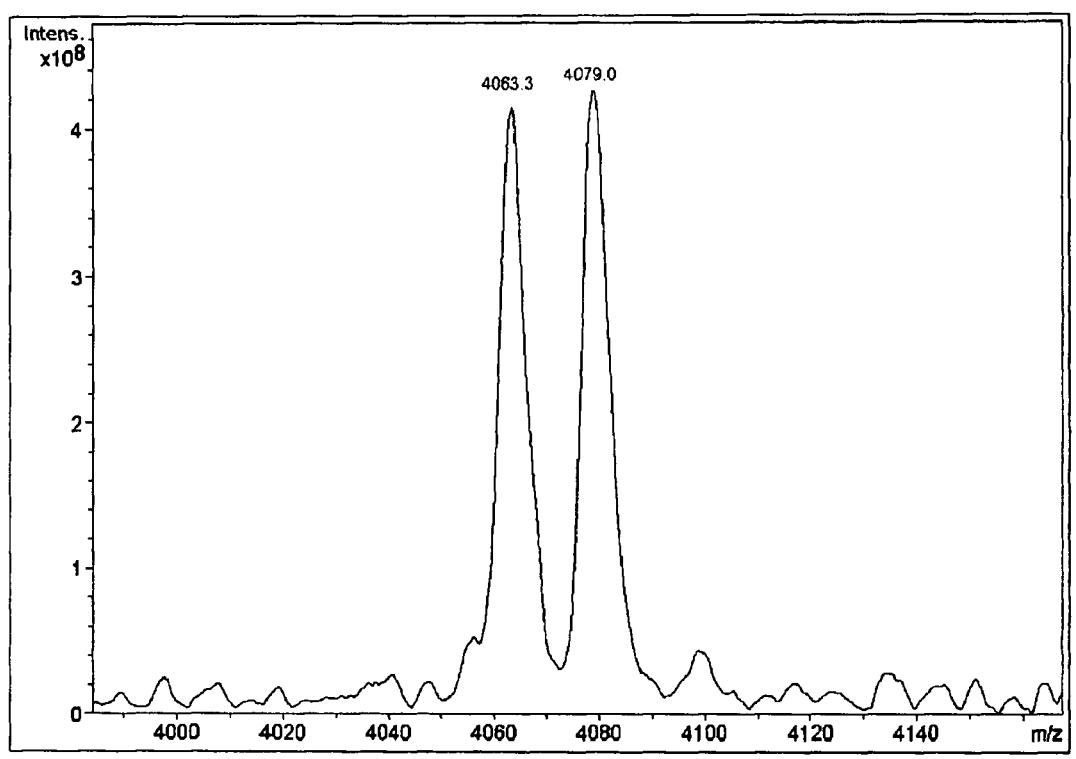
FIG. 4 shows the MALDI-TOF mass spectrum of the 13mer when the $2741^{st}$ base of the $4^{th}$ intron of human maspin gene is hetero (C/T).
Figure 5:
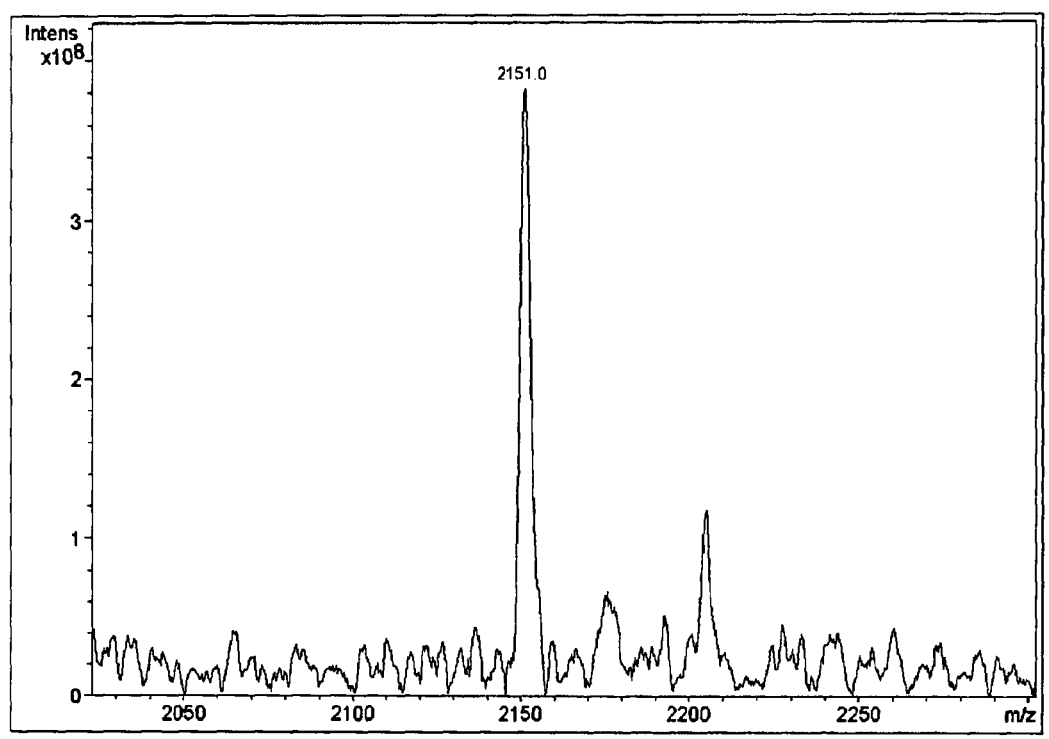
FIG. 5 shows the MALDI-TOF mass spectrum of the 7mer when the $2741^{st}$ base of the $4^{th}$ intron of human maspin gene is all changed into T (T/T).
Figure 6:
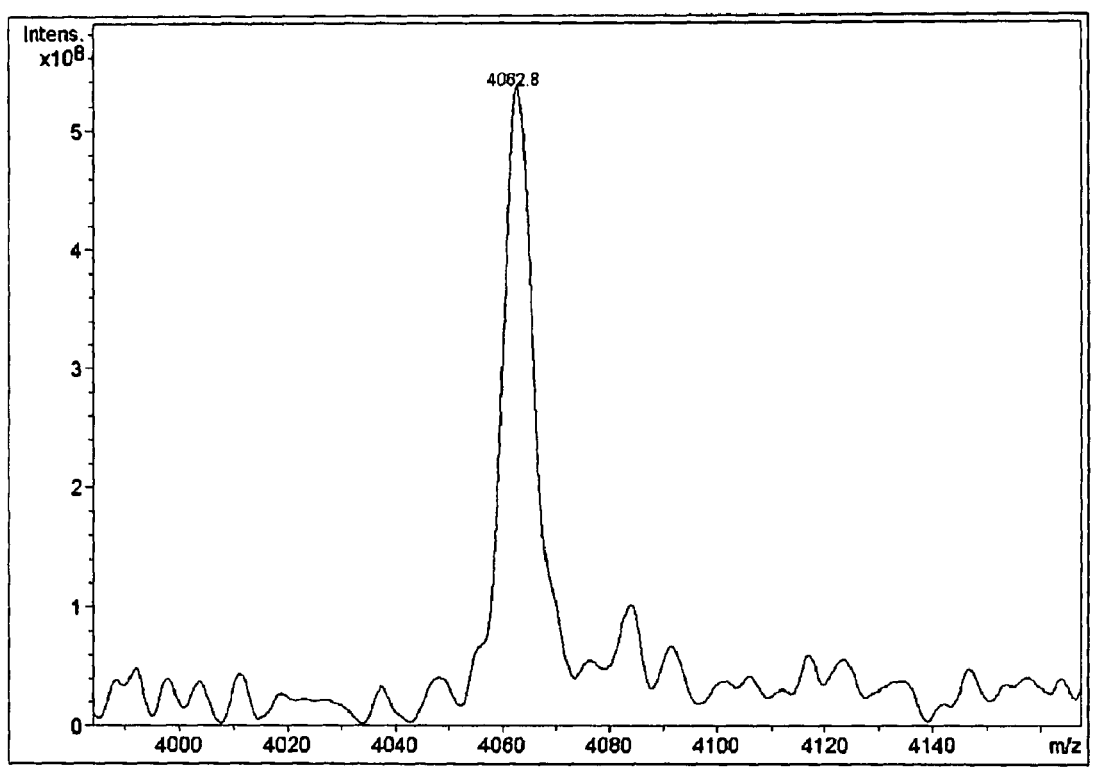
FIG. 6 shows the MALDI-TOF mass spectrum of the 13mer when the $2741^{st}$ base of the $4^{th}$ intron of human maspin gene is all changed into T (T/T).

When the $2741^{st}$ base of the $4^{th}$ intron is normal (C/C), the molecular weight of fragments obtained after enzyme cleavage is 2135.4 D (7mer) and 4078.6 D (13mer) D (see FIGS. 1 and 2). When the $2741^{st}$ base of the $4^{th}$ intron is hetero (C/T), the molecular weight of fragments is 2135.4 D, 2150.4 D (7mer) and 4078.6 D and 4062.6 D (13mer) (see FIGS. 3 and 4). When the $2741^{st}$ base of the $4^{th}$ intron is all changed into T (T/T), the molecular weight of fragments is 2150.4 D (7mer) and 4062.6 D (13mer) (see FIGS. 5 and 6).

EXAMPLE 2

Mutation of the $3597^{th}$ Base (rs1396782; 61002611th Base of Chromosome No. 18) of the $4^{th}$ Intron of Human Maspin (Serpinb5) Gene Known as Human Cancer Metastasis Inhibition Gene The sequence of template DNA is as follows.

(SEQ ID NO:6)
CTGGAGTATTATCCTTGCAGGCTTGATATGAAGcTTGAAATTTCTCCCCA

AAGAGATTTAGTTAACAGGCAAA

The bolded sequences are sites where the following primers 3 and 4 hybridize. The mutation represented by a small letter is a 'mutation sequence'.

Primer 3.
(SEQ ID NO:7)
5' GAGTATTATCCTTGCAGGCTTggatgATATGAAG 3' (34 mer)

Primer 4.
(SEQ ID NO:8)
5'-GCCTGTTAACTAAATCTCTTTGGGGAGAA 3' (29 mer)

The sites represented by small letters in the above primers are sequences that do not exist in template DNA, but Fok1 and BstF5I recognize them. The experimental method including the PCR reaction is the same as that of Example 1.

The sequences of fragments obtained through the PCR are as follows (5'→3').

(SEQ ID NO:9)
GAGTATTATCCTTGCAGGCTTggatgATATGAAG[C/T]TTGAAATTTCT

CCCCAAAGAGATTTAGTTAACAGGC (SEQ ID NO:10)
CTCATAATAGGAACGTCCGAAcctacTATACTTC[G/A]AACTTTAAAGA

GGGGTTTCTCTAAATCAATTGTCCG

The sites represented by small letters in the above sequences are restriction enzyme recognition sequences, the bolded sites are sequences of fragments obtained from restriction enzyme cleavage, and the bases represented by brackets ([ ]) are 'mutation sequences'. To the reactant were added FokI (NEB R109L) 1 U, BstF5I (NEB, V0031L) 1 U, 50 mM of potassium acetate, 20 mM of Tris-acetate, 10 mM of magnesium acetate, 1 mM of DTT (pH 7.9 @ 25° C.). The resulting solution was reacted at 25° C. for 2 hours, and consecutively at 45° C. for 2 hours.

Figure 7:
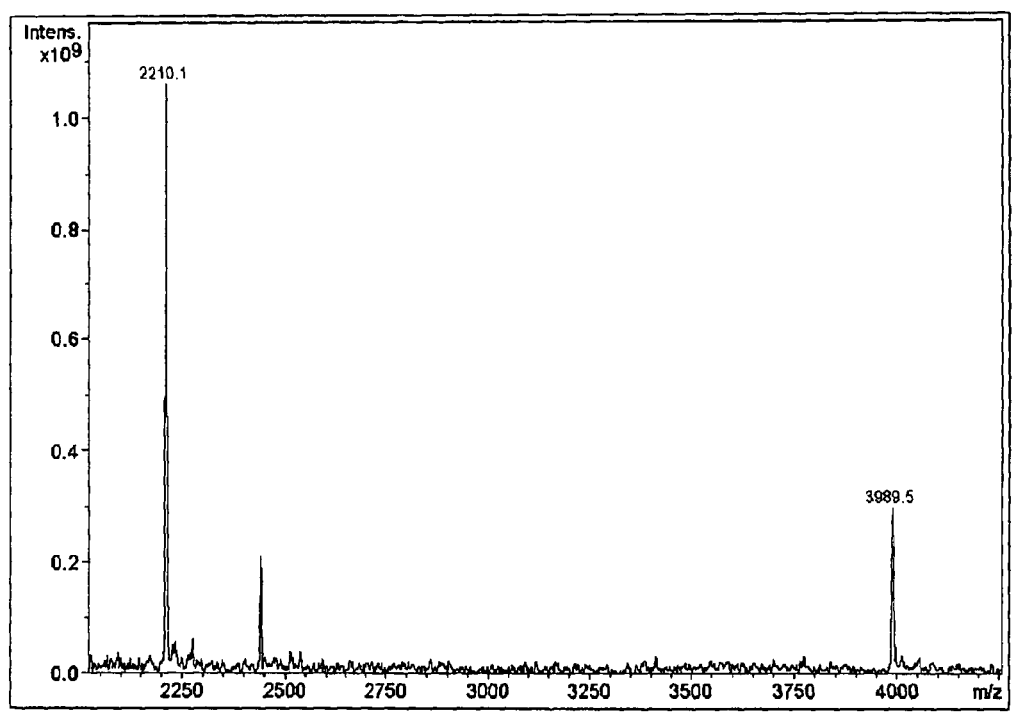
FIG. 7 shows the MALDI-TOF mass spectrum of the 7mer and the 13mer when the $3597^{th}$ base of the $4^{th}$ intron of human maspin gene is normal (C/C).
Figure 8:
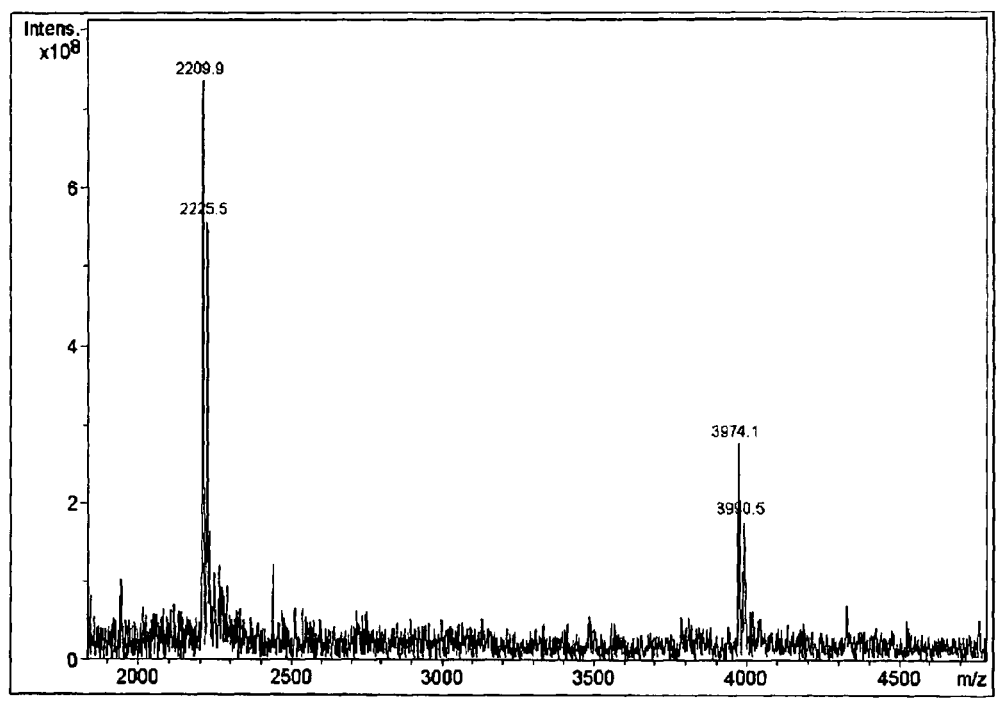
FIG. 8 shows the MALDI-TOF mass spectrum of the 7mer and the 13mer when the $3597^{th}$ base of the $4^{th}$ intron of human maspin gene is hetero (C/T).
Figure 9:
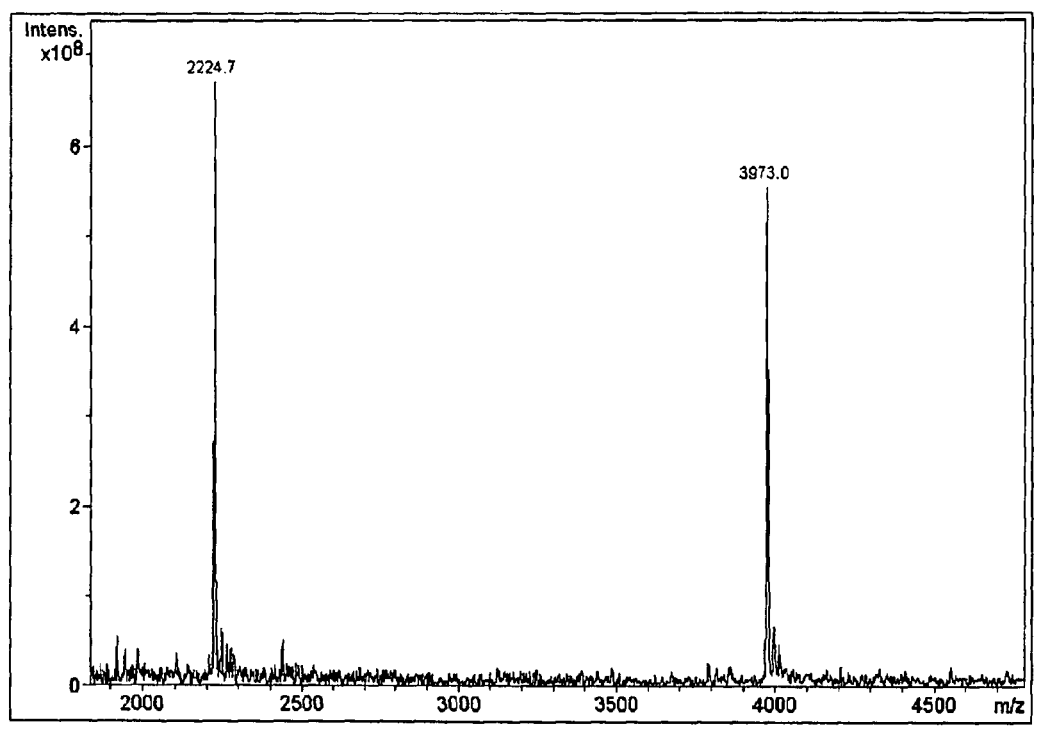
FIG. 9 shows the MALDI-TOF mass spectrum of the 7mer and the 13mer when the $3597^{th}$ base of the $4^{th}$ intron of human maspin gene is all changed into T (T/T).

When the $3597^{th}$ base of the $4^{th}$ intron is normal (C/C), the molecular weight of fragments obtained from enzyme cleavage is 2209.4 D (7mer) and 3988.6 D (13mer) (see FIG. 7). When the $3597^{th}$ base of the $4^{th}$ intron is hetero (C/T), the molecular weight of fragments is 2209.4 D, 2224.4 D (7mer), and 3988.6 D and 3972. 6 D (13mer) (see FIG. 8). When the $3597^{th}$ base of the $4^{th}$ intron is all changed into T (T/T), the molecular weight of fragments is 2224.4 D (7mer) and 3972. 6 D (13mer) (see FIG. 9).

EXAMPLE 3

Base Mutation of
Tyrosine-Methionine-Aspartate-Aspartate (YMDD)
Site of Hepatitis B Virus DNA Polymerase Mutations of YMDD site located in DNA polymerase gene of hepatitis B virus that causes hepatitis B to human were examined. Resistance to lamivudine that is used in a treatment of hepatitis B was generated by the mutation of YMDD site. It was known that resistance to lamivudine was generated when methionine (M) that is a codon No. 552 was changed into valine (V) or isoleucine (I).

1. PCR Amplification and Restriction Enzyme Cleavage

Hepatitis B virus DNA was isolated from 0.2 ml of serum using QIAamp blood kit (Qiagen, CA), and 2 ul of DNA was used in PCR amplification.

The sequence of Template DNA (5'→3') is as follows.

(SEQ ID NO:11)
TTCCCCCACTGTTTGGCTTTCAGTTATATGGATGATGTGGTATTGGGGGC

CAAGTCTGTA

The bolded sequences are sites where the following primers 5 and 6 are hybridized.

Primer 5.
(SEQ ID NO:12)
5'-TTCCCCCACTGTTTGGCTggatgTCAGTTAT-3' (31 mer)

Primer 6.
(SEQ ID NO:13)
5'-TACAGACTTGGCCCCCAATACCACATGATC-3' (30 mer)

The sequence represented by a small letter in the primer 5 is a recognition sequence of Fok1 and BstF5I, which is not included in template DNA rather artificially inserted. The bolded sequence in the primer 6 is an artificially changed sequence to prevent recognition by Fok1.

By using 18 ul of reaction solution containing 20 mM of Tris HCl (pH 8.4), 50 mM of KCl, 0.2 mM of dNTP, 0.4 U Platinum Taq Polymerase (Invitrogen, 10966-026), 10 pmol of the primer 5 and 10 pmol of the primer 6, the PCR reaction was performed under the following condition.

94° C., 2 min.

94° C., 15 sec. 50° C., 15 sec. 72° C., 30 sec. (10 cycles), 94° C., 15 sec. 55° C., 15 sec. 72° C., 30 sec. (35 cycles)

The sequences of fragments obtained through the PCR are as follows (5'→3').

```
                                                      (SEQ ID NO:14)
TTCCCCCACTGTTTGGCTggatgTCAGTTATATGGATCATGTGGTATTGG

GGCCAAGTCTGTA (SEQ ID NO:15)
AAGGGGGTGACAAACCGAcctacAGTCAATATACCTAGTACACCATAACC

CCCGGTTCAGACAT
```

The sites represented by small letters are sequences recognized by Fok1 and BstF5I, and the bolded sites are sequences of fragments obtained from restriction enzyme cleavage. The PCR products were mixed with FokI (NEB R109L) 1 U, BstF5I (NEB, V0031L) 1 U and 10 µl of reaction solution (50 mM potassium acetate, 20 mM Tris-acetate, 10 mM magnesium acetate, 1 mM DTT). The mixture solution was reacted at 37° C. for 2 hours, and then at 45° C. for 2 hours. The PCR products might be cleaved first by FokI at 37° C. for 2 hours, and then by BstF5I at 45° C. for 2 hours.

2. Purification & Desalination, and MALDI-TOF Mass Spectrometry

The experiment was performed by the same method as that of Example 1.

The calculative size of fragments obtained from enzyme cleavage precisely corresponds to the value measured by the actual molecular weight analysis, showing the difference of less than 0.1% (see Table 1). The sequences of presumed 13-mer fragments correspond to SEQ ID NOs. 34-38 of the sequence listing.

1. RT PCR

RNA of hepatitis C virus was isolated from 0.14 ml of serum using QIAamp viral RNA Mini kit (Qiagen, CA), and 10 µl of the RNA was used in RT PCR amplification.

Reaction solution containing 0.2 mM of dNTP, 0.4 uM of primer 2 and 10 µl of RNA was reacted at 65° C. for 5 minutes, and left on ice for 1 minute. The reaction solution was mixed with 20 mM of TrisHCl (pH 8.4), 50 mM of KCl, 4 mM of DTT, 0.4 uM of primer 1, 100 U SuperScript III RNase H-Reverse Transcriptase (Invitrogen, 18080-044), 20 U RNaseOUT (Invitrogen, 10777-019), 0.4 U Platinum Taq Polymerase (Invitrogen, 10966-026). Then, the RT PCR was performed using 25 µl of the resulting solution under the following condition.

50° C., 45 min.,
94° C., 2 sec.,
94° C., 15 sec. 55° C., 15 sec. 72° C., 30 sec. (35 cycles)
72° C., 5 min.

The sequence of template DNA (5'→3') is as follows.

```
                                                      (SEQ ID NO:16)
GCAGAAAGCGTCTAGCCATGGCGTTAGTATGAGTGTCGTGCAGCCTCCAG

GACCCCCCCTCCCGGGAGAGCCATAGTGGTCTGCGGAACCGGTGAGTACA

CCGGAATTGCCAGGACGACCGGGTCCTTTCTTGGATCAACCCGCTCAATG

CCTGGAGATTTGGGCGTGCCCCCGCAAGACTGCTAGCCGAGTAGTGTTGG

GTCGCGAAAGGCCTTGTGGTACTGCCTGATAGGGTGCTTGCGAG
```

TABLE 1

Presumption and observation mass of oligonucleotide by restriction enzyme cleavage of PCR product

| Genotype codon | Sequence of presumed fragment | | Mass of presumed fragment (Da) | | Mass of observed fragment (Da) | |
|---|---|---|---|---|---|---|
| No. 552 | 7 mer | 13 mer | 7 mer | 13 mer | 7 mer | 13 mer |
| YMDD | aTg AGTTATa | TCcAtATAACTGA | 2199.4 | 3997.6 | 2199.6 | 3998.0 |
| YVDD | aTg AGTTATg | TCcAcATAACTGA | 2215.4 | 3982.6 | 2215.9 | 3982.6 |
| YIDD | aTt AGTTATa | TCaAtATAACTGA | 2199.4 | 4021.6 | 2199.6 | 4021.8 |
| YIDD | aTc AGTTATa | TCgAtATAACTGA | 2199.4 | 4037.6 | 2199.6 | 4038.0 |
| YIDD | aTa AGTTATa | TCtAtATAACTGA | 2199.4 | 4012.6 | 2199.6 | 4012.6 |

In the above table, the resolution (difference between the observed mass and the presumed mass divided by the presumed mass) is less than 0.1%.

EXAMPLE 4

Mutation of 5' NCR (Non Coding Region) Site of Hepatitis C Virus

When interferon is used for treatment of chronic hepatitis C, different treatment effects are shown depending on genotypes of hepatitis C in human body. As a result, the examination of genotypes of hepatitis C virus in human body is required before use of interferon. In order to find out genotypes, the examination of mutation of 5' NCR is useful. In an embodiment of the present invention, a method for analyzing mutations of 5'NCR sites of hepatitis C virus is disclosed.

The bolded sequences are sites where the following primers 7 and 8 are hybridized.

```
Primer 7.
                                                      (SEQ ID NO:17)
5'-GCAGAAAGCGTCTAGCCATGGCGT-3'  (24 mer)

Primer 8.
                                                      (SEQ ID NO:18)
5'-CTCGCAAGCACCCTATCAGGCAGT-3'  (24 mer)
```

2. Nested PCR and Restriction Enzyme Cleavage

The above RT PCR reaction solution was diluted into 1/50. 2 ul of the diluted solution was mixed with 18 ul of reaction solution containing 20 mM of TrisHCl (pH 8.4), 50 mM KCl, 0.2 mM dNTP, 0.4 U Platinum Taq Polymerase (Invitrogen, 10966-026), 10 pmol of primers 9 and 10, 10 pmol of primers 11 and 12 and 10 pmol of primers 13 and 14. The following three types of PCR reaction and restriction enzyme treatment were performed using the mixture solution. The primers 9 and 10 were used in the reaction 1, the primers 11 and 12 in the reaction 2, and the primers 13 and 14 in the reaction 3. The PCR reaction temperature and time of the three reactions are as follows.

94° C., 5 min
94° C., 30 sec. 55° C., 30 sec. 72° C., 30 sec. (35 cycles)
72° C., 5 min.
Reaction 1

The PCR was performed on the RT-PCR solution using the primers 9 and 10. The sequence of template DNA (5'→3') is as follows.

(SEQ ID NO:19)
CGTCTAGCCATGGCGTTAGTATGAGTGTCGTGCAGCCTCCAGGACCCCCC

CTCCCGGGAGAGCCATAGTGGTCTGCGGAACCGGTGAGTACACCGGAATT

GCCAGGACGACCGGGTCCTTTCTTGGATCAACCCGCTCAATGCCTGGAGA

TTTGGGCGTGCCCCCGCAAGACTGCTAGCCGAGTAGTGTTGGGTCGCGAA

AGGCCTTGTGGTACTGCCTGATAGGG

The bolded sequences are sites where the following primers 9 and 10 are hybridized.

Primer 9.
                                        (SEQ ID NO:20)
    5'-CGTCTAGCCATGGCGTTAGggatgATGAGTGT-3' (32 mer)

Primer 10
                                        (SEQ ID NO:21)
    5'-CCCTATCAGGCAGTACCACAAGGC-3' (24 mer)

The sequences of fragments produced by the PCR are as follows (5'→3').

(SEQ ID NO:22)
CGTCTAGCCATGGCGTTAGggatgATGAGTGTCGTGCAGCCTCCAGGACC

CCCCCTCCCGGGAGAGCCATAGTGGTCTGCGGAACCGGTGAGTACACCGG

AATTGCCAGGACGACCGGGTCCTTTCTTGGATCAACCCGCTCAATGCCTG

GAGATTTGGGCGTGCCCCCGCAAGACTGCTAGCCGAGTAGTGTTGGGTCG

CGAAAGGCCTTGTGGTACTGCCTGATAGGG (SEQ ID NO:23)
CCCTATCAGGCAGTACCACAAGGCCTTTCGCGACCCAACACTACTCGGCT

AGCAGTCTTGCGGGGCACGCCCAAATCTCCAGGCATTGAGCGGGTTGAT

CCAAGAAAGGACCCGGTCGTCCTGGCAATTCCGGTGTACTCACCGGTTCC

GCAGACCACTATGGCTCTCCCGGGAGGGGGGGTCCTGGAGGCTGCACGAC

ACTCATCATCCCTAACGCCATGGCTAGACG

The sites represented by small letters are sequences recognized by FokI and BstF5I. The bolded sites are sequences of fragments generated by restriction enzyme cleavage (7mer and 13mer). The PCR products were mixed with FokI (NEB R109L) 1 U, BstF5I (NEB, V0031L) 1 U and 10 μl of reaction solution (50 mM potassium acetate, 20 mM Tris-acetate, 10 mM magnesium acetate, 1 mM DTT). The mixture solution was reacted at 37° C. for 2 hours, and at 45° C. for 2 hours. The PCR products might be cleaved by FokI at 37° C. for 2 hours, and then by BstF5I at 45° C. for 2 hours.

Reaction 2

The PCR was performed on the RT-PCR reaction solution using the primers 11 and 12. The sequence of Template DNA (5'3') is as follows.

(SEQ ID NO:24)
GTGGTCTGCGGAACCGGTGAGTACACCGGAATTGCCAGGACGACCGGGTC

CTTTCTTGGATCAACCCGCTCAATGCCTGGAGATTTGGGCGTGCCCCCGC

AAGACTGCTAGCCGAGTAGRGTTGGGTRGCGAA

The bolded sequences are sites where the following primers 11 and 12 are hybridized.

Primer 11.
                                        (SEQ ID NO:25)
5'-GTGGTCTGtccaacCGGTGAGTACACCGGAAT-3' (32 mer)

Primer 12.
                                        (SEQ ID NO:26)
5'-TTCGCRACCCAACRCTACtccaacggtcCGGCTAG-3' (35 mer)

The bases represented by R are adenine (A) or guanine (G). The mixture of two primers containing each base is used.

The sequences of fragments generated through the PCR are as follows (5'→3').

(SEQ ID NO:27)
GTGGTCTGtccaacCGGTGAGTACACCGGAATTGCCAGGACGACCGGGTC

CTTTCTTGGATCAACCCGCTCAATGCCTGGAGATTTGGGCGTGCCCCCGC

AAGACTGCTAGCCGgaccgttggaGTAGRGTTGGGTRGCGAA (SEQ ID NO:28)
TTCGCRACCCAACRCTACTCCAACGGTCCGGCTAGCAGTCTTGCGGGGGC

ACGCCCAAATCTCCAGGCATTGAGCGGGTTGATCCTTGAAAGGACCCGGT

CGTCCTGGCAATTCCGGTGTACTCACCGGTTGGACAGACCAC

The sites represented by small letters are sequences recognized by MmeI and AvaII, and the bolded sites are sequences of fragments generated by restriction enzyme cleavage (13mer, 18mer, 24mer and 19mer). The PCR products were mixed with MmeI (NEB R0637L) 1.5 U, 50 uM SAM and 1X reaction solution (50 mM potassium acetate, 20 mM Tris-acetate, 10 mM magnesium acetate, 1 mM DTT, pH 7.9) 10 ul. The mixture solution was reacted at 37° C. for 2 hours, and then AvaII (NEB, R0153S) 1.5 U was added thereto. The resulting solution was reacted at 37° C. for 2 hours. MmeI and AvaII might be simultaneously added to the mixture solution.

Reaction 3

The PCR was performed on the RT-PCR reaction solution using the primer 13 and 14. The sequence of Template DNA (5'→3') is as follows.

(SEQ ID NO:29)
GACIGGGTCCTTTCTTGGATCAACCCGCTCAATGCCTGGAGATTTGGGCG

TGCCCCCGC

The bolded sequences are sites where the following primers 13 and 14 are hybridized.

Primer 13.
                                        (SEQ ID NO:30)
    5'-GACIGGGTCCTggatgTCTTGGA-3' (23 mer)

```
Primer 14.
                                             (SEQ ID NO:31)
5'-GCGGGGGCACggatgCCCAAAT- 3'  (22 mer)
```

The bases represented by I are Inosine.

The sequences of fragments generated by the PCR are as follows (5'→3').

```
                                             (SEQ ID NO:32)
GACIGGGTCCTggatgTCTTGGATC AACCCGCTCAATGC CTGGAGATT TGGGcatccGTGCCCCCGC (SEQ ID NO:33)
CTGICCCAGGAcctacAGGAACCTAGTTGG GCGAGTTACGGACC TCTA AACCCgtaggCACGGGGCG
```

The sites represented by small letters are sequences recognized by Fok1 and BstF5I, and the bolded sites are sequences generated by restriction enzyme cleavage. The generated fragments are two 7mers, two 13mers, and two 14mers. The PCR products were mixed with FokI (NEB R109L) 1 U, BstF5I (NEB, V0031L) 1 U and 10 μl of reaction solution (50 mM potassium acetate, 20 mM Tris-acetate, 10 mM magnesium acetate, 1 mM DTT). The mixture solution was reacted at 37° C. for 2 hours, and at 45° C. for 2 hours. The fragments were cleaved first by FokI at 37° C. for 2 hours, and then by BstF5I at 45° C. for 2 hours.

2. Purification & Desalination, and MALDI-TOF Mass Spectrometry

Three types of PCR and restriction enzyme cleavage reaction solution were purified by the same method as that of Example 1, and then the molecular weight was measured.

The size of fragments generated from Reactions 1 (Table 2), 2 (Table 3) and 3 (Table 4) is shown in Tables 2-4. Genotypes of hepatitis C are determined according to the size of fragments by ready reckoner shown in Tables 2-4.

TABLE 2

| Genotype | 7 mer | 13 mer |
|---|---|---|
| 1a | 2216.4 | 3983.6 |
| 1b | 2216.4 | 3983.6 |
| 1c | 2216.4 | 3983.6 |
| 3a | 2216.4 | 3983.6 |
| 3b | 2216.4 | 3983.6 |
| 3c | 2216.4 | 3983.6 |
| 3d | 2216.4 | 3983.6 |
| 3e | 2216.4 | 3983.6 |
| 3f | 2216.4 | 3983.6 |
| 6b | 2216.4 | 3983.6 |
| 7a | 2216.4 | 3983.6 |
| 7b | 2216.4 | 3983.6 |
| 7c | 2216.4 | 3983.6 |
| 2' | 2216.4 | 3989.6 |
| 5a | 2216.4 | 3989.6 |
| 1b | 2216.4 | 3998.6 |
| 1d | 2216.4 | 3998.6 |
| 1e | 2216.4 | 3998.6 |
| 1f | 2216.4 | 3998.6 |
| 2a | 2216.4 | 3998.6 |
| 2b | 2216.4 | 3998.6 |
| 2c | 2216.4 | 3998.6 |
| 2d | 2216.4 | 3998.6 |
| 2e | 2216.4 | 3998.6 |
| 2' | 2216.4 | 3998.6 |
| 4h | 2216.4 | 3998.6 |
| 6a | 2216.4 | 3998.6 |
| 7d | 2216.4 | 3998.6 |
| 1b | 2231.4 | 3967.6 |
| 4g | 2231.4 | 3967.6 |
| 4k | 2231.4 | 3967.6 |
| 2a | 2231.4 | 3982.6 |
| 4a | 2231.4 | 3982.6 |
| 4b | 2231.4 | 3982.6 |
| 4c | 2231.4 | 3982.6 |
| 4d | 2231.4 | 3982.6 |
| 4e | 2231.4 | 3982.6 |
| 4e' | 2231.4 | 3982.6 |
| 4f | 2231.4 | 3982.6 |
| 4f' | 2231.4 | 3982.6 |

TABLE 3

| Genotype | 13 mer | 18 mer | Genotype | 14 mer | 19 mer |
|---|---|---|---|---|---|
| 1a | 4049.6 | 5556.6 | 2a | 4337.8 | 5891.8 |
| 1b | 4049.6 | 5556.6 | 2e | 4337.8 | 5891.8 |
| 1c | 4049.6 | 5556.6 | 4b | 4337.8 | 5891.8 |
| 1d | 4049.6 | 5556.6 | 4e' | 4337.8 | 5891.8 |
| 1e | 4049.6 | 5556.6 | 1a | 4352.8 | 5875.8 |
| 1f | 4049.6 | 5556.6 | 1c | 4352.8 | 5875.8 |
| 6b | 4049.6 | 5556.6 | 1d | 4352.8 | 5875.8 |
| 7a | 4049.6 | 5556.6 | 1e | 4352.8 | 5875.8 |
| 7b | 4049.6 | 5556.6 | 2a | 4352.8 | 5875.8 |
| 4a | 4049.6 | 5572.6 | 2b | 4352.8 | 5875.8 |
| 6a | 4064.6 | 5540.6 | 2c | 4352.8 | 5875.8 |
| 7c | 4064.6 | 5540.6 | 2d | 4352.8 | 5875.8 |
| 7d | 4064.6 | 5540.6 | 2'-1 | 4352.8 | 5875.8 |
| 4f' | 4065.6 | 5541.6 | 2'-2 | 4352.8 | 5875.8 |
| 4e' | 4064.6 | 5556.6 | 3a | 4352.8 | 5875.8 |
| 4f | 4065.6 | 5557.6 | 3b | 4352.8 | 5875.8 |
| 4g | 4065.6 | 5557.6 | 3d | 4352.8 | 5875.8 |
| 5a | 4080.6 | 5525.6 | 3e | 4352.8 | 5875.8 |
| 3b | 4080.6 | 5541.6 | 4c | 4352.8 | 5875.8 |
| 4b | 4080.6 | 5541.6 | 4d | 4352.8 | 5875.8 |
| 4c | 4080.6 | 5541.6 | 4f | 4352.8 | 5875.8 |
| 4d | 4080.6 | 5541.6 | 4f' | 4352.8 | 5875.8 |
| 4e | 4080.6 | 5541.6 | 4g | 4352.8 | 5875.8 |
| 4h | 4080.6 | 5541.6 | 6a | 4352.8 | 5875.8 |
| 4k | 4080.6 | 5541.6 | 6b | 4352.8 | 5875.8 |
| 2d | 4088.6 | 5515.6 | 7c | 4353.8 | 5876.8 |
| 2b | 4088.6 | 5530.6 | 1b | 4368.8 | 5860.8 |
| 3f | 4096.6 | 5526.6 | 1f | 4368.8 | 5860.8 |
| 2a | 4104.6 | 5500.6 | 3c | 4368.8 | 5860.8 |
| 2c | 4104.6 | 5500.6 | 3f | 4368.8 | 5860.8 |
| 2e | 4104.6 | 5500.6 | 4a | 4368.8 | 5860.8 |
| 2' | 4104.6 | 5500.6 | 4e | 4368.8 | 5860.8 |
| 2' | 4104.6 | 5500.6 | 4h | 4368.8 | 5860.8 |
| 3a | 4111.6 | 5510.6 | 4k | 4368.8 | 5860.8 |
| 3c | 4111.6 | 5510.6 | 5a | 4368.8 | 5860.8 |
| 3d | 4111.6 | 5510.6 | 7a | 4368.8 | 5860.8 |
| 3e | 4111.6 | 5510.6 | 7b | 4368.8 | 5860.8 |
|  |  |  | 7d | 4368.8 | 5860.8 |

TABLE 4

| HCV nt-140 Forward | | | HCV nt-140 Reverse | | | nt-140 Intra (14 mer) | | |
| --- | --- | --- | --- | --- | --- | --- | --- | --- |
| Genotype | 7 mer | 13 mer | Genotype | 7 mer | 13 mer | Genotype | Forward | Reverse |
| 6a | 2191.4 | 4053.6 | 2'-2 | 2144.4 | 4110.6 | 2d | 4247.8 | 4392.8 |
| 6b | 2191.4 | 4053.6 | 4f | 2144.4 | 4110.6 | 2a | 4247.8 | 4408.8 |
| 7d | 2191.4 | 4053.6 | 5a | 2144.4 | 4110.6 | 2c | 4247.8 | 4408.8 |
| 1f | 2191.4 | 4062.6 | 1a | 2144.4 | 4125.6 | 2e | 4247.8 | 4408.8 |
| 1a | 2191.4 | 4078.6 | 1b | 2144.4 | 4125.6 | 2'-1 | 4247.8 | 4408.8 |
| 1b | 2191.4 | 4078.6 | 1c | 2144.4 | 4125.6 | 2'-2 | 4247.8 | 4408.8 |
| 1e | 2191.4 | 4078.6 | 1d | 2144.4 | 4125.6 | 1d | 4248.8 | 4368.8 |
| 4a | 2191.4 | 4078.6 | 1e | 2144.4 | 4125.6 | 1f | 4287.8 | 4368.8 |
| 4b | 2191.4 | 4078.6 | 1f | 2144.4 | 4125.6 | 3a | 4256.8 | 4414.8 |
| 4e' | 2191.4 | 4078.6 | 6a | 2144.4 | 4125.6 | 3c | 4256.8 | 4414.8 |
| 7a | 2191.4 | 4078.6 | 6b | 2144.4 | 4125.6 | 3e | 4256.8 | 4414.8 |
| 7b | 2191.4 | 4078.6 | 7a | 2144.4 | 4125.6 | 2b | 4562.0 | 4714.0 |
| 7c | 2191.4 | 4078.6 | 7b | 2144.4 | 4125.6 | 1a | 4272.8 | 4368.8 |
| 3d | 2200.4 | 4044.6 | 7c | 2144.4 | 4125.6 | 1b | 4272.8 | 4368.8 |
| 4g | 2200.4 | 4044.6 | 7d | 2144.4 | 4125.6 | 1e | 4272.8 | 4368.8 |
| 4k | 2200.4 | 4053.6 | 3a | 2159.4 | 4078.6 | 1e | 4272.8 | 4368.8 |
| 3b | 2200.4 | 4069.6 | 3c | 2159.4 | 4078.6 | 4a | 4272.8 | 4368.8 |
| 3c | 2200.4 | 4069.6 | 3d | 2159.4 | 4078.6 | 4e' | 4272.8 | 4368.8 |
| 3e | 2200.4 | 4069.6 | 3e | 2159.4 | 4078.6 | 7a | 4272.8 | 4368.8 |
| 4e | 2206.4 | 4037.6 | 3b | 2159.4 | 4094.6 | 7b | 4272.8 | 4368.8 |
| 1b | 2206.4 | 4062.6 | 3f | 2159.4 | 4094.6 | 3d | 4570.0 | 4744.0 |
| 1c | 2206.4 | 4062.6 | 4c | 2159.4 | 4094.6 | 3f | 4546.0 | 4744.0 |
| 2'-2 | 2206.4 | 4062.6 | 4d | 2159.4 | 4094.6 | 3b | 4272.8 | 4384.8 |
| 4f | 2206.4 | 4062.6 | 4e | 2159.4 | 4094.6 | 4b | 4272.8 | 4384.8 |
| 5a | 2206.4 | 4062.6 | 4f | 2159.4 | 4094.6 | 4c | 4272.8 | 4384.8 |
| 1b | 2215.4 | 4053.6 | 4h | 2159.4 | 4094.6 | 4d | 4272.8 | 4384.8 |
| 2a | 2215.4 | 4053.6 | 4k | 2159.4 | 4094.6 | 4f | 4272.8 | 4384.8 |
| 2b | 2215.4 | 4053.6 | 4a | 2159.4 | 4109.6 | 5a | 4272.8 | 4384.8 |
| 2c | 2215.4 | 4053.6 | 4e' | 2159.4 | 4109.6 | 4e | 4296.8 | 4384.8 |
| 2d | 2215.4 | 4053.6 | 4b | 2184.4 | 4070.6 | 4g | 4586.0 | 4714.0 |
| 2e | 2215.4 | 4053.6 | 4g | 2184.4 | 4070.6 | 4k | 4287.8 | 4384.8 |
| 2'-1 | 2215.4 | 4053.6 | 2a | 2193.4 | 4061.6 | 4f | 4562.0 | 4384.8 |
| 3f | 2215.4 | 4053.6 | 2b | 2193.4 | 4061.6 | 4h | 4562.0 | 4384.8 |
| 4c | 2215.4 | 4053.6 | 2e | 2193.4 | 4061.6 | 6a | 4586.0 | 4698.0 |
| 4d | 2215.4 | 4053.6 | 2d | 2193.4 | 4076.6 | 6b | 4586.0 | 4698.0 |
| 4f | 2215.4 | 4053.6 | 2c | 2209.4 | 4046.6 | 7d | 4586.0 | 4698.0 |
| 4h | 2215.4 | 4053.6 | 2'-1 | 2209.4 | 4046.6 | 1b | 4288.8 | 4353.8 |
| 3a | 2216.4 | 4054.6 | 2c | 2209.4 | 4030.6 | 7c | 4288.8 | 4353.8 |
| 1d | 2215.4 | 4078.6 | | | | | | |

In an embodiment of the present invention, the analysis misled by errors in the conventional method for detecting mutations may be identified, and various mutations of adjacent base within 32 bases may be simultaneously examined. When there are various genotypes in an individual having mutations, whether mutations in different sites exist in one genotype at the same time or exist with mixed in two or more genotypes may be distinguished. In addition, mutations resulting from deletion or insertion can be detected.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A primer for analyzing a gene mutation comprising a primer binding sequence 1, a restriction enzyme recognition sequence and a primer binding sequence 2, wherein two or more single stranded polynucleotide fragments that contain at least one mutation sequence respectively and have sizes of 2-32 bases are produced by amplifying with the primer and cleaving with two or more restriction enzymes recognizing the restriction enzyme recognition sequence, and the primer is selected from the group consisting of SEQ ID NO: 2, 7, 12, 20, 25 and 30.

2. The primer according to claim 1, wherein the restriction enzymes have different optimum temperatures.

3. The primer according to claim 2, wherein a first restriction enzyme is Fok1 and a second restriction enzyme is BstF5.

4. The primer according to claim 1, wherein the primer is used for mutation analysis of the $2741^{ST}$ or $3597^{TH}$ base site of the $4^{TH}$ intron of human maspin gene or for mutation analysis of lamivudine resistant hepatitis B virus or hepatitis C virus.

* * * * *

SEQUENCE LISTING

<160> NUMBER OF SEQ ID NOS: 38

<210> SEQ ID NO 1
<211> LENGTH: 69
<212> TYPE: DNA
<213> ORGANISM: Homo sapiens

<400> SEQUENCE: 1
gtttcacttg ataaagcaat aaaatgctat tcacagctgc atgaggctac acccttcttt    60

-continued tgaatgcag                                                             69

<210> SEQ ID NO 2
<211> LENGTH: 34
<212> TYPE: DNA
<213> ORGANISM: Artificial Sequence
<220> FEATURE:
<223> OTHER INFORMATION: Forward primer for 4th intron region of maspin
      gene

<400> SEQUENCE: 2
tcacttgata aagcaataaa aggatggcta ttca                                 34

<210> SEQ ID NO 3
<211> LENGTH: 28
<212> TYPE: DNA
<213> ORGANISM: Artificial Sequence
<220> FEATURE:
<223> OTHER INFORMATION: Reverse primer for 4th intron region of maspin
      gene

<400> SEQUENCE: 3
cattcaaaag aagggtgtag cctcatgc                                        28

<210> SEQ ID NO 4
<211> LENGTH: 67
<212> TYPE: DNA
<213> ORGANISM: Artificial Sequence
<220> FEATURE:
<223> OTHER INFORMATION: PCR product for 4th intron region of maspin
      gene

<400> SEQUENCE: 4
tcacttgata aagcaataaa aggatggcta ttcayagctg catgaggcta cacccttctt     60
ttgaatg                                                               67

<210> SEQ ID NO 5
<211> LENGTH: 67
<212> TYPE: DNA
<213> ORGANISM: Artificial Sequence
<220> FEATURE:
<223> OTHER INFORMATION: PCR product for 4th intron region of maspin
      gene

<400> SEQUENCE: 5
cattcaaaag aagggtgtag cctcatgcag ctrtgaatag ccatccttttt attgctttat    60 caagtga                                                               67

<210> SEQ ID NO 6
<211> LENGTH: 73
<212> TYPE: DNA
<213> ORGANISM: Homo sapiens

<400> SEQUENCE: 6
ctggagtatt atccttgcag gcttgatatg aagcttgaaa tttctcccca aagagattta    60
gttaacaggc aaa                                                        73

<210> SEQ ID NO 7
<211> LENGTH: 34
<212> TYPE: DNA
<213> ORGANISM: Artificial Sequence
<220> FEATURE:
<223> OTHER INFORMATION: Forward primer for 4th intron region of maspin
      gene -continued

<400> SEQUENCE: 7
gagtattatc cttgcaggct tggatgatat gaag                                34

<210> SEQ ID NO 8
<211> LENGTH: 29
<212> TYPE: DNA
<213> ORGANISM: Artificial Sequence
<220> FEATURE:
<223> OTHER INFORMATION: Reverse primer for 4th intron region of maspin
      gene

<400> SEQUENCE: 8
gcctgttaac taaatctctt tggggagaa                                      29

<210> SEQ ID NO 9
<211> LENGTH: 71
<212> TYPE: DNA
<213> ORGANISM: Artificial Sequence
<220> FEATURE:
<223> OTHER INFORMATION: PCR product for 4th intron region of maspin
      gene

<400> SEQUENCE: 9
gagtattatc cttgcaggct tggatgatat gaagyttgaa atttctcccc aaagagattt    60
agttaacagg c                                                         71

<210> SEQ ID NO 10
<211> LENGTH: 71
<212> TYPE: DNA
<213> ORGANISM: Artificial Sequence
<220> FEATURE:
<223> OTHER INFORMATION: PCR product for 4th intron region of maspin
      gene

<400> SEQUENCE: 10
gcctgttaac taaatctctt tggggagaaa tttcaarctt catatcatcc aagcctgcaa    60
ggataatact c                                                         71

<210> SEQ ID NO 11
<211> LENGTH: 60
<212> TYPE: DNA
<213> ORGANISM: Hepatitis B virus

<400> SEQUENCE: 11
ttcccccact gtttggcttt cagttatatg gatgatgtgg tattgggggc caagtctgta    60

<210> SEQ ID NO 12
<211> LENGTH: 31
<212> TYPE: DNA
<213> ORGANISM: Artificial Sequence
<220> FEATURE:
<223> OTHER INFORMATION: Forward primer for HBV

<400> SEQUENCE: 12
ttcccccact gtttggctgg atgtcagtta t                                   31

<210> SEQ ID NO 13
<211> LENGTH: 30
<212> TYPE: DNA
<213> ORGANISM: Artificial Sequence
<220> FEATURE:
<223> OTHER INFORMATION: Reverse primer for HBV

<400> SEQUENCE: 13

```
tacagacttg gcccccaata ccacatgatc                                     30

<210> SEQ ID NO 14
<211> LENGTH: 64
<212> TYPE: DNA
<213> ORGANISM: Artificial Sequence
<220> FEATURE:
<223> OTHER INFORMATION: PCR product for HBV

<400> SEQUENCE: 14
ttcccccact gtttggctgg atgtcagtta tatggatcat gtggtattgg gggccaagtc   60
tgta                                                                 64

<210> SEQ ID NO 15
<211> LENGTH: 64
<212> TYPE: DNA
<213> ORGANISM: Artificial Sequence
<220> FEATURE:
<223> OTHER INFORMATION: PCR product for HBV

<400> SEQUENCE: 15
tacagacttg gcccccaata ccacatgatc catataactg acatccagcc aaacagtggg   60
ggaa                                                                 64

<210> SEQ ID NO 16
<211> LENGTH: 244
<212> TYPE: DNA
<213> ORGANISM: Artificial Sequence
<220> FEATURE:
<223> OTHER INFORMATION: 5'- noncoding region of HCV

<400> SEQUENCE: 16
gcagaaagcg tctagccatg gcgttagtat gagtgtcgtg cagcctccag gacccccccct  60 cccgggagag ccatagtggt ctgcggaacc ggtgagtaca ccggaattgc caggacgacc  120
gggtcctttc ttggatcaac ccgctcaatg cctggagatt tgggcgtgcc cccgcaagac  180
tgctagccga gtagtgttgg gtcgcgaaag gccttgtggt actgcctgat agggtgcttg  240
cgag                                                                244

<210> SEQ ID NO 17
<211> LENGTH: 24
<212> TYPE: DNA
<213> ORGANISM: Artificial Sequence
<220> FEATURE:
<223> OTHER INFORMATION: Forward primer for 5'- noncoding region of HCV

<400> SEQUENCE: 17
gcagaaagcg tctagccatg gcgt                                           24

<210> SEQ ID NO 18
<211> LENGTH: 24
<212> TYPE: DNA
<213> ORGANISM: Artificial Sequence
<220> FEATURE:
<223> OTHER INFORMATION: Reverse primer for 5'- noncoding region of HCV

<400> SEQUENCE: 18
ctcgcaagca ccctatcagg cagt                                           24

<210> SEQ ID NO 19
<211> LENGTH: 226
<212> TYPE: DNA
<213> ORGANISM: Artificial Sequence
```

```
<220> FEATURE:
<223> OTHER INFORMATION: 5'- noncoding region of HCV

<400> SEQUENCE: 19
cgtctagcca tggcgttagt atgagtgtcg tgcagcctcc aggacccccc ctcccgggag    60
agccatagtg gtctgcggaa ccggtgagta caccggaatt gccaggacga ccgggtcctt   120
tcttggatca acccgctcaa tgcctggaga tttgggcgtg ccccccgcaag actgctagcc  180 gagtagtgtt gggtcgcgaa aggccttgtg gtactgcctg ataggg                  226

<210> SEQ ID NO 20
<211> LENGTH: 32
<212> TYPE: DNA
<213> ORGANISM: Artificial Sequence
<220> FEATURE:
<223> OTHER INFORMATION: Forward primer

<400> SEQUENCE: 20
cgtctagcca tggcgttagg gatgatgagt gt                                  32

<210> SEQ ID NO 21
<211> LENGTH: 24
<212> TYPE: DNA
<213> ORGANISM: Artificial Sequence
<220> FEATURE:
<223> OTHER INFORMATION: Reverse primer

<400> SEQUENCE: 21
ccctatcagg cagtaccaca aggc                                           24

<210> SEQ ID NO 22
<211> LENGTH: 230
<212> TYPE: DNA
<213> ORGANISM: Artificial Sequence
<220> FEATURE:
<223> OTHER INFORMATION: Nested PCR product for 5'- noncoding region of
      HCV

<400> SEQUENCE: 22
cgtctagcca tggcgttagg gatgatgagt gtcgtgcagc ctccaggacc ccccctcccg    60
ggagagccat agtggtctgc ggaaccggtg agtacaccgg aattgccagg acgaccgggt   120
cctttcttgg atcaacccgc tcaatgcctg gagatttggg cgtgccccccg caagactgct  180 agccgagtag tgttgggtcg cgaaaggcct tgtggtactg cctgataggg              230

<210> SEQ ID NO 23
<211> LENGTH: 230
<212> TYPE: DNA
<213> ORGANISM: Artificial Sequence
<220> FEATURE:
<223> OTHER INFORMATION: Nested PCR product for 5'- noncoding region of
      HCV

<400> SEQUENCE: 23
ccctatcagg cagtaccaca aggcctttcg cgacccaaca ctactcggct agcagtcttg    60 cggggggcacg cccaaatctc caggcattga gcgggttgat ccaagaaagg acccggtcgt  120
cctggcaatt ccggtgtact caccggttcc gcagaccact atggctctcc cgggaggggg   180
ggtcctggag gctgcacgac actcatcatc cctaacgcca tggctagacg               230

<210> SEQ ID NO 24
<211> LENGTH: 133
<212> TYPE: DNA
```

<213> ORGANISM: Artificial Sequence
<220> FEATURE:
<223> OTHER INFORMATION: 5'- noncoding region of HCV

<400> SEQUENCE: 24

```
gtggtctgcg gaaccggtga gtacaccgga attgccagga cgaccgggtc ctttcttgga      60
tcaacccgct caatgcctgg agatttgggc gtgcccccgc aagactgcta gccgagtagr     120
gttgggtrgc gaa                                                        133
```

<210> SEQ ID NO 25
<211> LENGTH: 32
<212> TYPE: DNA
<213> ORGANISM: Artificial Sequence
<220> FEATURE:
<223> OTHER INFORMATION: Forward primer

<400> SEQUENCE: 25

```
gtggtctgtc caaccggtga gtacaccgga at                                    32
```

<210> SEQ ID NO 26
<211> LENGTH: 35
<212> TYPE: DNA
<213> ORGANISM: Artificila sequence
<220> FEATURE:
<223> OTHER INFORMATION: Reverse primer

<400> SEQUENCE: 26

```
ttcgcraccc aacrctactc caacggtccg gctag                                 35
```

<210> SEQ ID NO 27
<211> LENGTH: 142
<212> TYPE: DNA
<213> ORGANISM: Artificial Sequence
<220> FEATURE:
<223> OTHER INFORMATION: Nested PCR product for 5'- noncoding region of
      HCV

<400> SEQUENCE: 27

```
gtggtctgtc caaccggtga gtacaccgga attgccagga cgaccgggtc ctttcttgga      60
tcaacccgct caatgcctgg agatttgggc gtgcccccgc aagactgcta gccggaccgt     120
tggagtagrg ttgggtrgcg aa                                              142
```

<210> SEQ ID NO 28
<211> LENGTH: 142
<212> TYPE: DNA
<213> ORGANISM: Artificila sequence
<220> FEATURE:
<223> OTHER INFORMATION: Nested PCR product for 5'- noncoding region of
      HCV

<400> SEQUENCE: 28

```
ttcgcraccc aacrctactc caacggtccg gctagcagtc ttgcggggggc acgcccaaat      60 ctccaggcat tgagcgggtt gatccttgaa aggacccggt cgtcctggca attccggtgt     120
actcaccggt tggacagacc ac                                              142
```

<210> SEQ ID NO 29
<211> LENGTH: 59
<212> TYPE: DNA
<213> ORGANISM: Artificila sequence
<220> FEATURE:
<223> OTHER INFORMATION: 5'- noncoding region of HCV
<220> FEATURE:
<221> NAME/KEY: misc_feature

```
<222> LOCATION: 4
<223> OTHER INFORMATION: n = inosine

<400> SEQUENCE: 29
gacngggtcc tttcttggat caacccgctc aatgcctgga gatttgggcg tgccccgc        59

<210> SEQ ID NO 30
<211> LENGTH: 23
<212> TYPE: DNA
<213> ORGANISM: Artificial Sequence
<220> FEATURE:
<223> OTHER INFORMATION: Forward primer
<220> FEATURE:
<221> NAME/KEY: misc_feature
<222> LOCATION: 4
<223> OTHER INFORMATION: n = inosine

<400> SEQUENCE: 30
gacngggtcc tggatgtctt gga                                              23

<210> SEQ ID NO 31
<211> LENGTH: 22
<212> TYPE: DNA
<213> ORGANISM: Artificial Sequence
<220> FEATURE:
<223> OTHER INFORMATION: Reverse primer

<400> SEQUENCE: 31 gcggggcac ggatgcccaa at                                                22

<210> SEQ ID NO 32
<211> LENGTH: 67
<212> TYPE: DNA
<213> ORGANISM: Artificial Sequence
<220> FEATURE:
<223> OTHER INFORMATION: Nested PCR product for 5'- noncoding region of
      HCV
<220> FEATURE:
<221> NAME/KEY: misc_feature
<222> LOCATION: 4
<223> OTHER INFORMATION: n = inosine

<400> SEQUENCE: 32
gacngggtcc tggatgtctt ggatcaaccc gctcaatgcc tggagatttg ggcatccgtg      60
ccccccgc                                                               67

<210> SEQ ID NO 33
<211> LENGTH: 68
<212> TYPE: DNA
<213> ORGANISM: Artificial Sequence
<220> FEATURE:
<223> OTHER INFORMATION: Nested PCR product for 5'- noncoding region of
      HCV
<220> FEATURE:
<221> NAME/KEY: misc_feature
<222> LOCATION: 65
<223> OTHER INFORMATION: n = inosine

<400> SEQUENCE: 33 gcggggcac ggatgcccaa atctccaggc attgagcggg ttgatccaag gacatccagg       60 acccngtc                                                               68

<210> SEQ ID NO 34
<211> LENGTH: 13
<212> TYPE: DNA
<213> ORGANISM: Artificial Sequence
<220> FEATURE:
```

```
<223> OTHER INFORMATION: Oligonucleotide obtained by restriction enzyme
      cleavage of PCR  product

<400> SEQUENCE: 34
tccatataac tga                                                          13

<210> SEQ ID NO 35
<211> LENGTH: 13
<212> TYPE: DNA
<213> ORGANISM: Artificial sequence
<220> FEATURE:
<223> OTHER INFORMATION: Oligonucleotide obtained by restriction enzyme
      cleavage of PCR  product

<400> SEQUENCE: 35
tccacataac tga                                                          13

<210> SEQ ID NO 36
<211> LENGTH: 13
<212> TYPE: DNA
<213> ORGANISM: Artificial Sequence
<220> FEATURE:
<223> OTHER INFORMATION: Oligonucleotide obtained by restriction enzyme
      cleavage of PCR  product

<400> SEQUENCE: 36
tcaatataac tga                                                          13

<210> SEQ ID NO 37
<211> LENGTH: 13
<212> TYPE: DNA
<213> ORGANISM: Artificial Sequence
<220> FEATURE:
<223> OTHER INFORMATION: Oligonucleotide obtained by restriction enzyme
      cleavage of PCR  product

<400> SEQUENCE: 37
tcgatataac tga                                                          13

<210> SEQ ID NO 38
<211> LENGTH: 13
<212> TYPE: DNA
<213> ORGANISM: Artificial Sequence
<220> FEATURE:
<223> OTHER INFORMATION: Oligonucleotide obtained by restriction enzyme
      cleavage of PCR  product

<400> SEQUENCE: 38
tctatataac tga                                                          13
```